US009623055B2

(12) United States Patent
Nieuwdorp et al.

(10) Patent No.: US 9,623,055 B2
(45) Date of Patent: *Apr. 18, 2017

(54) METHOD FOR PREVENTING AND/OR TREATING INSULIN RESISTANCE

(71) Applicants: Academisch Medisch Centrum, Amsterdam (NL); Caelus Pharmaceuticals B.V., Zegveld (NL)

(72) Inventors: Max Nieuwdorp, Amsterdam (NL); Willem Meindert De Vos, Ede (NL)

(73) Assignees: Academisch Medisch Centrum, Amsterdam (NL); Caelus Pharmaceuticals B.V., Zegveld (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/207,335

(22) Filed: Jul. 11, 2016

(65) Prior Publication Data

US 2016/0317589 A1 Nov. 3, 2016

Related U.S. Application Data

(63) Continuation of application No. 14/241,851, filed as application No. PCT/NL2012/050592 on Aug. 30, 2012, now Pat. No. 9,433,650.

(60) Provisional application No. 61/528,931, filed on Aug. 30, 2011.

(30) Foreign Application Priority Data

Aug. 30, 2011 (NL) ...................................... 2007319

(51) Int. Cl.
| | |
|---|---|
| *A01N 63/00* | (2006.01) |
| *A61K 35/74* | (2015.01) |
| *A23L 2/52* | (2006.01) |
| *A61K 35/744* | (2015.01) |
| *A23L 29/00* | (2016.01) |
| *A23L 33/135* | (2016.01) |
| *A23K 10/16* | (2016.01) |
| *A61K 9/00* | (2006.01) |
| *A61K 35/00* | (2006.01) |

(52) U.S. Cl.
CPC .............. *A61K 35/74* (2013.01); *A23K 10/16* (2016.05); *A23L 2/52* (2013.01); *A23L 29/065* (2016.08); *A23L 33/135* (2016.08); *A61K 9/0095* (2013.01); *A61K 35/744* (2013.01); *A23V 2002/00* (2013.01); *A61K 2035/11* (2013.01)

(58) Field of Classification Search
None
See application file for complete search history.

(56) References Cited

U.S. PATENT DOCUMENTS

| | | | |
|---|---|---|---|
| 5,902,578 A | 5/1999 | Halpin-Dohnalek et al. | |
| 6,227,863 B1 | 5/2001 | Spector | |
| 6,645,530 B1 | 11/2003 | Borody | |
| 2004/0076614 A1* | 4/2004 | Schur ..................... | A61K 45/06 424/93.4 |
| 2007/0258953 A1 | 11/2007 | Duncan et al. | |
| 2008/0069861 A1 | 3/2008 | Brown et al. | |
| 2014/0294774 A1 | 10/2014 | Nieuwdorp | |

FOREIGN PATENT DOCUMENTS

| | | |
|---|---|---|
| EP | 1917869 A1 | 5/2008 |
| WO | 2004085628 A1 | 10/2004 |
| WO | 2008076696 A2 | 6/2008 |
| WO | 2010036876 A2 | 4/2010 |
| WO | 2011043654 A1 | 4/2011 |
| WO | 2011145516 A1 | 11/2011 |
| WO | 2012142605 A1 | 10/2012 |
| WO | 2013032328 A1 | 3/2013 |

OTHER PUBLICATIONS

Engels et al., Frontiers Microbiol., 7(713):1-12 (2016).*
Kavuncuoglu et al., Peritoneal Dialysis Internat., 30(1):112-121 (2010).*
Ma et al., J. Hepatology, 49:821-830 (2008).*
Yun et al., J. App. Microbiol., 107:1681-1686 (2009).*
Flint et al., Env. Microbiol., 9(5):1101-1111 (2007).*
Williams et al., Diabetes, 2000, pp. 626-32, vol. 49.
Suthar et al., Bacterial contamination in drinking water: a case study in rural areas of northern Rajasthan, India, Environ Monit Assess., Nov. 21, 2008, vol. 159, No. 1-4, pp. 43-40.
Gao et al., Diabetes, 2009, pp. 1409-17, vol. 58.
Kavuncuoglu F. et al., First Reported Case of Alcaligenes faecalis Peritonitis. Pent Dial Int., Jan.-Feb. 2010, vol. 30, No. 1, pp. 118-119.
Netherlands Search Report dated Mar. 26, 2012 for Netherlands Application No. NL2007319, 4 pages.
International Search Report dated Oct. 15, 2012 for International Application No. PCT/NL2012/050592, 3 pages.
Examination Report for Singapore Patent Application No. 11201401811W, dated Mar. 16, 2015.

(Continued)

*Primary Examiner* — Thomas J Visone
(74) *Attorney, Agent, or Firm* — TraskBritt P.C.

(57) ABSTRACT

Described is the use of *Eubacterium hallii* et rel. and/or *Alcaligenes faecalis* et rel., as well as pharmaceutical, food, or feed compositions comprising these bacteria as a medicament, in particular, for preventing and/or treating insulin resistance and/or insulin resistance-related complications such as metabolic syndrome, dyslipidemia and type 2 diabetes mellitus, as well as insulin resistance in endocrine diseases (e.g., obese subjects with type 1 diabetes mellitus, Cushing's disease and lipodystrophy syndromes. Also described is a method for preventing and/or treating insulin resistance and/or insulin resistance-related complications such as dyslipidemia and type 2 diabetes mellitus as well as insulin resistance in endocrine diseases (e.g., obese subjects with type 1 diabetes mellitus, Cushing's disease and lipodystrophy syndromes) in a subject in need thereof, the method comprising the step of increasing the level of *Eubacterium hallii* et rel. and/or *Alcaligenes faecalis* et rel. in the small intestine.

24 Claims, No Drawings

(56) References Cited

OTHER PUBLICATIONS

Ahanci et al., Heightened efficacy of nitric oxide-based therapies in type II diabetes mellitus and metabolic syndrome, Oct. 14, 2008, pp. H2388-H2398, Am J Physical Heart Circ Physiol 295.
Notification of Third Chinese Office Action dated Jan. 9, 2017, application No. 201280053708.2, english translation included.
Anderson et al., a comparison of NO And N2O production by the Autotrophic Nitrifier Nitromonas europaea and the -leterotrophic Nitrifier Alcalignees faeclis, Aug. 11, 1993, pp. 3525-3533, Applied Environmental Microbiology, vol. 59 No. 11.
Duncan et al., Lacatate —Utilizing Bacteria Isolated from Human Feces, That Produce Butyrate as a Major Fermentation Product; Jun. 14, 2004, pp. 5810-5817, Applied and Environmental Microbiology vol. 70 No. 10.

* cited by examiner

METHOD FOR PREVENTING AND/OR TREATING INSULIN RESISTANCE

CROSS-REFERENCE TO RELATED APPLICATIONS

This application is continuation of U.S. patent application Ser. No. 14/241,851, filed Jun. 6, 2014, pending, which application is a national phase entry under 35 U.S.C. §371 of International Patent Application PCT/NL2012/050592, filed Aug. 30, 2012, designating the United States of America and published in English as International Patent Publication WO 2013/032328 A1 on Mar. 7, 2013, which claims the benefit under Article 8 of the Patent Cooperation Treaty and under 35 U.S.C. §119(e) to U.S. Provisional Patent Application Ser. No. 61/528,931, filed Aug. 30, 2011, and to The Netherlands Patent Application Serial No. 2007319, filed Aug. 30, 2011.

TECHNICAL FIELD

The disclosure relates to the field of medicine. This disclosure is directed to bacteria of the taxa *Eubacterium hallii* et rel. and/or *Alcaligenes faecalis* et rel., optionally used in a pharmaceutical, food, or feed composition, for use as a medicament, in particular, for preventing and/or treating insulin resistance and/or insulin resistance-related complications such as metabolic syndrome, dyslipidemia and type 2 diabetes mellitus.

BACKGROUND

Obesity is primarily a consequence of detrimental nutritional and physical habits against an unfavorable genetic background. It is a major risk factor for the development of common medical conditions such as the metabolic syndrome, type 2 diabetes mellitus and cardiovascular disease. As a metabolically active organ, the human intestine contains a dense and diverse community of micro-organisms, dominated by over a thousand different bacterial species. There is growing evidence for the role of intestinal microbiota in host metabolism.

The phyla that account for the vast majority of intestinal microbiota include the Gram-negative Bacteroidetes, Proteobacteria and Verrucomicrobia, as well as the Gram-positive Firmicutes and Actinobacteria. It was previously shown that the gut microbiota contributes to the development of diet-induced obesity in mice. The colonic microbiota in obese mice appeared to be characterized by a lower microbial diversity and an enrichment in carbohydrate and lipid-utilizers. Putatively, the short chain fatty acids acetate, propionate and butyrate produced by specific gut bacteria could serve as a signal that directly influences host hepatic and peripheral insulin sensitivity. On the other hand, recent research showed that lower gut microbial diversity in mice was associated with endotoxemia-induced chronic inflammation and subsequent development of insulin resistance.

In humans, altered colonic microbiota have been correlated to obesity, but consensus regarding specific bacterial groups of species and evidence for a causative role is lacking. As metabolically healthy and unhealthy obese phenotypes exist based on the absence or presence of insulin resistance, published reports on associations between intestinal microbiota composition and human obesity seem to be compromised by heterogeneity in the obese phenotype, various confounding factors e.g., diet, medication use) and developing methods to analyze the intestinal microbiota. This is particularly true for the small intestinal microbiota that is relatively inaccessible but is exposed to a large surface. It has been found that the microbial diversity of the small intestine is smaller than that of the colon and is notably enriched in bacteria belonging to the *Lactobacillales* and *Veillonella* spp. (Booijnk et al., 2010, *Env. Microbiol.* 12:3213-27). Thus, there is a need in the art to find further medicaments suitable to treat and/or prevent insulin resistance and/or type 2 diabetes mellitus, preferably medicaments that can be easily incorporated in the patient's lifestyle, for example, in the form of food compositions for daily consumption.

DISCLOSURE

The disclosure relates to *Eubacterium hallii* et rel. and/or *Alcaligenes faecalis* et rel. for use in preventing and/or treating insulin resistance and/or insulin resistance-related conditions like metabolic syndrome, dyslipidemia and type 2 diabetes mellitus, as well as insulin resistance in endocrine diseases (e.g., obese subjects with type 1 diabetes mellitus, Cushing's disease and lipodystrophy syndromes).

In a second aspect, provided is a pharmaceutical, food, or feed composition comprising *Eubacterium hallii* et rel. and/or *Alcaligenes faecalis* et rel. for use in preventing and/or treating insulin resistance and/or related conditions like metabolic syndrome, dyslipidemia and type 2 diabetes mellitus, as well as insulin resistance in endocrine diseases (e.g., obese subjects with type 1 diabetes mellitus, Cushing's disease and lipodystrophy syndromes).

In a further aspect, this disclosure pertains to a method for preventing and/or treating insulin resistance and/or related conditions in a subject in need thereof, the method comprising the step of increasing the level of *Eubacterium hallii* et rel. and/or *Alcaligenes faecalis* et rel. in the small intestine. The level of *Eubacterium hallii* et rel. and/or *Alcaligenes faecalis* et rel. in the small intestine may be increased by a method selected from the group consisting of administering an effective amount of *Eubacterium hallii* et rel. and/or *Alcaligenes faecalis* et rel. to the subject, and administering an effective amount of a compound capable of increasing the level of *Eubacterium hallii* et rel. and/or *Alcaligenes faecalis* et rel. in the small intestine.

In another aspect, the disclosure pertains to a pharmaceutical, food, or feed composition comprising *Alcaligenes faecalis* et rel. The composition may be a drink. The pharmaceutical, food, or feed composition comprising *Alcaligenes faecalis* et rel. may be for use as a medicament.

DEFINITIONS

As used herein, the term "insulin resistance" has its common meaning in the art. Insulin resistance is a physiological condition where the natural hormone insulin becomes less effective at lowering blood sugars. The resulting increase in blood glucose may raise levels outside the normal range and cause adverse health effects such as metabolic syndrome, dyslipidemia and subsequently type 2 diabetes mellitus. The term "insulin resistance-related complications" and "insulin resistance-related conditions" as used herein encompass, without limitation, metabolic syndrome, dyslipidemia and type 2 diabetes mellitus, as well as insulin resistance in endocrine diseases (e.g., obese subjects with type 1 diabetes mellitus, Cushing's disease and lipodystrophy syndromes).

The addition "et rel." behind the genus-like group name (level 2 group name) stands for "et relatives," indicating all relatives of this phylogenetic group, i.e., those indicated in Table 3 of WO 2011/043654 (which is herein incorporated by reference), in the column headed "level 3." This information, including the indicated 16S rRNA gene sequences, can be used to develop specific PCR primers or LCR probes to detect the one or more members of these groups. In some literature, the addition "et rel." is replaced by "-like" to indicate the fact that the group includes more than one related species. However, this is a rather ambiguous designation and hence all terms with "et rel." are clearly defined in Table 3 of the incorporated WO 2011/043654, which has also been published by Rajilic-Stojaniovic et al. 2007, *Environ. Microbiol.* 9(9):2125-2136).

In the context of the disclosure, a subject may be an animal or a human being. Preferably, the subject is a human being. A "healthy subject," as referred to herein, does not suffer from insulin resistance and/or diabetes mellitus, and, preferably, does not suffer from any conditions or diseases of the gastrointestinal tract, and, more preferably, does not suffer from any known conditions or diseases. Preferably, a "healthy subject," as referred to herein, has a Body Mass Index (BMI) in the range of between 18.5 and 24.9 $kg/m^2$.

As used herein, the level of bacteria of the taxa *Eubacterium hallii* et rel. and/or *Alcaligenes faecalis* et rel. in a sample, e.g., an intestinal sample (e.g., duodenal or fecal), is increased when it is significantly higher than the level of one or more bacteria in a control sample, e.g., an intestinal control sample (e.g., duodenal or fecal). It is also considered increased when the level of bacteria of the taxa *Eubacterium hallii* et rel. and/or *Alcaligenes faecalis* et rel. in a sample is at least 5%, such as 10%, 15%, 20%, 25%, 30%, 35%, 40%, 45%, 50% higher than the bacteria of the taxa *Eubacterium hallii* et rel. and/or *Alcaligenes faecalis* et rel. in the control sample. The "control sample," as used herein, refers to a sample taken from a subject receiving treatment by administration of bacteria of the taxa *Eubacterium hallii* et rel. and/or *Alcaligenes faecalis* et rel. prior to administration of bacteria of the taxa *Eubacterium hallii* et rel. and/or *Alcaligenes faecalis* et rel., optionally in an effective amount.

As used herein, the term "effective amount" refers to a quantity sufficient to achieve a desired therapeutic and/or prophylactic effect, e.g., an amount that results in the treatment and/or prevention of insulin resistance and/or related complications like dyslipidemia and type 2 diabetes mellitus as well as insulin resistance in endocrine diseases (e.g., obese subjects with type 1 diabetes mellitus, Cushing's disease and lipodystrophy syndromes). In the context of therapeutic or prophylactic applications, the amount of bacteria administered to the subject will depend on the type and severity of the disease or condition and on the characteristics of the subject, such as general health, age, sex, body weight and tolerance to drugs. It will also depend on the degree, severity and type of disease or condition. The skilled artisan will be able to determine appropriate dosages depending on these and other factors. The bacteria can also be administered in combination with one or more additional therapeutic compounds. For example, with the phrase a "therapeutically effective amount" of the bacteria is meant levels of the bacteria that lead to an improvement of the physiological effects of a disease or condition associated with insulin resistance and/or related complications like dyslipidemia and type 2 diabetes mellitus, as well as insulin resistance in endocrine diseases (e.g., obese subjects with type 1 diabetes mellitus, Cushing's disease and lipodystrophy syndromes). The skilled person will be capable of determining when such disease or condition has been treated and/or prevented.

In this document and in its claims, the verb "to comprise" and its conjugations is used in its non-limiting sense to mean that items following the word are included, but items not specifically mentioned are not excluded. In addition, the verb "to consist" may be replaced by "to consist essentially of," meaning that a composition of this disclosure may comprise additional component(s) than the ones specifically identified, those additional component(s) not altering the unique characteristics of the disclosure.

In addition, reference to an element by the indefinite article "a" or "an" does not exclude the possibility that more than one of the element is present, unless the context clearly requires that there be one and only one of the elements. The indefinite article "a" or "an" thus usually means "at least one."

DETAILED DESCRIPTION

We have found a causal role of the small intestinal microbiota in insulin resistance and dyslipidemia. Eighteen male subjects with newly diagnosed metabolic syndrome underwent small intestine biopsies and subsequent polyethylene-glycol bowel lavage through duodenal tube insertion followed by random assignment to either allogenic or autologous fecal transplantation. In the allogenic fecal transplantation group that was performed on nine subjects, the fecal material was derived from a healthy and lean donor. The autologous transplantation group included the nine other subjects and these received their own fecal material.

It was found that the subjects of the allogenic group were characterized by different sigmoidal gut microbiota compared to those of the autologous group as determined by analysis with a phylogenetic microarray (the Human Intestinal Tract Chip, HITChip) (Rajilic-Stojanovic, 2009, *Environ. Microbiol.* 11(7):1736-1751). Fasting levels of TG-rich lipoproteins (TG/ApoB ratio) were significantly reduced in the subjects in the allogenic group with no effect after autologous feces infusion. Although the weight of the subjects remained stable, six weeks after feces transplantation, an improvement in both peripheral (Rd) and hepatic insulin sensitivity (suppression of EGP) was found six weeks in the allogenic group while no significant changes were observed in the autologous treatment group.

We have identified changes in small intestinal microbiota between subjects receiving allogenic or autologous fecal transplantation. Comparing the small intestinal microbiota composition at baseline and after six weeks in the allogenic group showed an increased abundance of bacteria related to the ileum-inhabitant *Alcaligenes faecalis* and the butyrate-producing *Eubacterium hallii*. Notably, the latter butyrate-producer was almost two-fold reduced following infusion in the autologous group. Bacteria belonging to *Eubacterium hallii* et rel. include relatively fast-growing anaerobes. They have the metabolic capacity to convert lactate into butyrate in a process that needs acetate (Munoz-Tamayo et al., 2011, *FEMS Microbiol. Ecolo.* 76:615-624). Lactate and acetate are abundant metabolites in the upper intestinal tract that is colonized by, among others, *streptococci* and *lactobacilli* that can produce these compounds (Booijink et al., 2010, vide supra). However, it may be a specific embodiment of the disclosure to include the substrates lactate and acetate to the formulation containing bacteria belonging to the taxon *Eubacterium hallii* et rel. Bacteria related to *Alcaligenes faecalis* (belonging to the taxon *Alcaligenes faecalis* et rel.) are facultative anaerobic bacteria that degrade a variety of substrates—they have the unusual capacity to produce nitrous and nitric oxide under low oxygen conditions in the presence of ammonia (Anderson et al., 1993, *Appl. Environ. Microbiol.* 95:3525-33). As these conditions are met in the upper intestine, it is feasible that *Alacaligenes faecalis* produces nitric oxide. It has been proposed that nitric oxide is a therapy for the treatment of patients with type 2 diabetes and metabolic syndrome (Ahanchi et al., 2008, *Am. J. Physiol. Heart Circ. Physiol.* 295:H2388-98). However, delivery of nitrous oxide via its production by intestinal bacteria has not been described.

Thus, the disclosure relates to bacteria of the taxon *Eubacterium hallii* et rel. and/or bacteria of the taxon *Alcaligenes faecalis* et rel. for use in preventing and/or treating insulin resistance and/or insulin resistance-related complications such as metabolic syndrome, dyslipidemia and type 2 diabetes mellitus as well as insulin resistance in endocrine diseases (e.g., obese subjects with type 1 diabetes mellitus, Cushing's disease or lipodystrophy syndromes. In another embodiment, the present disclosure relates to bacteria of the taxon *Eubacterium hallii* et rel. and/or bacteria of the taxon *Alcaligenes faecalis* et rel. for use in preventing and/or treating a clinical condition in a mammal, such as human, which results from the endogenous hormone insulin becoming less effective at lowering blood sugars and subsequent plasma cholesterol profiles. Non-limiting examples of such clinical conditions include metabolic syndrome, dyslipidemia and type 2 diabetes mellitus as well as insulin resistance in endocrine diseases (e.g., obese subjects with type 1 diabetes mellitus, Cushing's disease and lipodystrophy syndromes). Bacteria of either of the taxa may be used alone as a medicament for the indicated purposes, or bacteria of the taxon *Eubacterium hallii* et rel. and bacteria of the taxon *Alcaligenes faecalis* et rel. may be used together as a medicament. Moreover, a combination of any one of these taxa of bacteria or bacteria of either taxa together may be used with currently used therapeutic agents in clinical practice (e.g., biguanides, sulfonureum derivates, PPAR gamma agonists, DPPIV inhibitors and injectable medication like GLP1 agonist and/or exogenous short-/long-acting insulin).

The disclosure also relates to a pharmaceutical, food, or feed composition comprising *Eubacterium hallii* et rel. and/or *Alcaligenes faecalis* et rel. for use in preventing and/or treating insulin resistance and/or related complications like dyslipidemia and type 2 diabetes mellitus. The pharmaceutical, food or feed composition preferably comprises an effective amount of *Eubacterium hallii* et rel. and/or *Alcaligenes faecalis* et rel. Preferably, the pharmaceutical, food or feed composition comprises in total between about $10^6$ and about $10^{12}$, preferably between about $10^8$ and about $10^{12}$, bacteria of the taxon *Eubacterium hallii* et rel. and/or bacteria of the taxon *Alcaligenes faecalis* et rel. Preferably, the bacteria are contained in a daily dose.

In another aspect, the disclosure pertains to a pharmaceutical, food, or feed composition comprising *Alcaligenes faecalis* et rel., optionally for use as a medicament. Such composition may comprise a carrier, such as an inert carrier.

Preferably, the composition referred to herein is for enteral or oral administration. A composition for enteral or oral administration may be either a food composition, feed composition, or a pharmaceutical composition. Such food composition, feed composition, or pharmaceutical composition does not include fecal compositions or compositions derived from fecal compositions.

A pharmaceutical composition will usually comprise a carrier, such as a pharmaceutical carrier, in addition to bacteria of the taxon *Eubacterium hallii* et rel. and/or bacteria of the taxon *Alcaligenes faecalis* et rel. The carrier is preferably an inert carrier. The preferred form depends on the intended mode of administration and (therapeutic) application. A pharmaceutical carrier can be any compatible, nontoxic substance suitable to deliver bacteria of the taxon *Eubacterium hallii* et rel. and/or bacteria of the taxon *Alcaligenes faecalis* et rel. to the gastro-intestinal tract of a subject. For example, sterile water, or inert solids may be used as a carrier usually complemented with a pharmaceutically acceptable adjuvant, buffering agent, dispersing agent, and the like. A composition will either be in liquid, e.g., a stabilized suspension of bacteria of the taxon *Eubacterium hallii* et rel. and/or bacteria of the taxon *Alcaligenes faecalis* et rel., or in solid forms, e.g., a powder of lyophilized bacteria of the taxon *Eubacterium hallii* et rel. and/or bacteria of the taxon *Alcaligenes faecalis* et rel. In case of lyophilization, a cryoprotectant such as lactose, threhalose or glycogen can be envisaged. For example, for oral administration, bacteria of the taxon *Eubacterium hallii* et rel. and/or bacteria of the taxon *Alcaligenes faecalis* et rel. can be administered in solid dosage forms, such as capsules, tablets, and powders, or in liquid dosage forms, such as elixirs, syrups, and suspensions. Bacteria of the taxon *Eubacterium hallii* et rel. and/or bacteria of the taxon *Alcaligenes faecalis* et rel. can be encapsulated in capsules such as gelatin capsules, together with inactive ingredients and powdered carriers, such as, e.g., glucose, lactose, sucrose, mannitol, starch, cellulose or cellulose derivatives, magnesium stearate, stearic acid, sodium saccharin, talcum, magnesium carbonate and the like.

A preferred composition according to the disclosure is suitable for consumption by a subject, which is preferably a human or a non-human animal. Such compositions may be in the form of a food supplement or a food or food composition (herein jointly referred to as "food composition"), which, besides bacteria of the taxon *Eubacterium hallii* et rel. and/or bacteria of the taxon *Alcaligenes faecalis* et rel., also contains a suitable food base. Alternatively, such composition may be in the form of a feed supplement or a fodder or feed composition (herein jointly referred to as "feed composition"). A food or food composition or feed composition is herein understood to include a liquid for human or non-human animal consumption, i.e., a drink or beverage. A food or food composition or feed composition may be a solid, semi-solid and/or liquid food or food composition and, in particular, may be a dairy product, such as a fermented dairy product, including, but not limited to a yogurt, a yogurt-based drink or buttermilk. Such a food or food composition or feed composition may be prepared in a manner known per se, for example, by adding bacteria of the taxon *Eubacterium hallii* et rel. and/or bacteria of the taxon *Alcaligenes faecalis* et rel. to a suitable food, food base, or feed base, in a suitable amount. Similarly, this may include the use of these bacteria in capsulated form as described above since they have to pass the low pH of the stomach. This may also be a preferred way so as to reduce the traces of butyrate that are associated with the growth of bacteria belonging to the taxon *Eubacterium hallii* et rel. and may produce off-flavor in a food or food composition. In another embodiment, bacteria of the taxon *Eubacterium hallii* et rel. and/or bacteria of the taxon *Alcaligenes faecalis* et rel. may be used in or for the preparation of a food or food composition or feed composition, e.g., by fermentation. In doing so, bacteria of the taxon *Eubacterium hallii* et rel. and/or bacteria of the taxon *Alcaligenes faecalis* et rel. may be used in a manner known per se for the preparation of such fermented foods or food compositions or fermented feed compositions, e.g., in a manner known per se for the preparation of fermented dairy products using lactic acid bacteria. In such methods, bacteria of the taxon *Eubacterium hallii* et rel. and/or bacteria of the taxon *Alcaligenes faecalis* et rel. may be used in addition to a micro-organism usually used, and/or may replace one or more or part of a micro-organism usually used.

Preferably, the above compositions will contain bacteria of the taxon *Eubacterium hallii* et rel. and/or bacteria of the taxon *Alcaligenes faecalis* et rel. in amounts that allow for convenient (oral) administration as indicated above, e.g., as or in one or more doses per day or per week. In particular, a preparation may contain a unit dose of bacteria of the taxon *Eubacterium hallii* et rel. and/or bacteria of the taxon *Alcaligenes faecalis* et rel.

In a further aspect, the disclosure relates to a method for preventing and/or treating insulin resistance and/or related complications like dyslipidemia and type 2 diabetes mellitus in a subject in need thereof, the method comprising the step of increasing the level of *Eubacterium hallii* et rel. and/or *Alcaligenes faecalis* et rel. in the small intestine.

The level of bacteria of the taxon *Eubacterium hallii* et rel. and/or bacteria of the taxon *Alcaligenes faecalis* et rel. may be measured by determining the levels of nucleic acid sequences, amino acid sequences and/or metabolites specific for one or more bacteria, preferably the level of nucleic acid sequences specific for one or more bacteria.

The level of one or more bacteria may preferably be measured by determining the level of specific nucleic acid sequences in a test sample derived from the small intestine, which nucleic acid sequences are preferably 16S rRNA gene sequences of bacteria of the taxon *Eubacterium hallii* et rel. and/or bacteria of the taxon *Alcaligenes faecalis* et rel., more preferably, one or more variable regions of the 16S rRNA gene sequences, e.g., one or more of the variable regions V1 and/or V6 of the 16S rRNA gene sequences.

The level of *Eubacterium hallii* et rel. and/or *Alcaligenes faecalis* et rel. in the small intestine may be increased by a method selected from the group consisting of administering an effective amount of *Eubacterium hallii* et rel. and/or *Alcaligenes faecalis* et rel. to the subject, and administering an effective amount of a compound capable of increasing the level of *Eubacterium hallii* et rel. and/or *Alcaligenes faecalis* et rel. in the small intestine.

Compounds capable of increasing the level of *Eubacterium hallii* et rel. in the small intestine may include, without limitation, lactate and acetate. Alternatively, *Eubacterium hallii* et rel. may be administered in combination with lactic acid-producing bacteria such as *Lactobacillus* spp. and *Bifidobacterium* spp. The lactic acid producing bacteria may be present in a fermented food product such as yogurt or a yogurt drink per se, and *Eubacterium hallii* et rel. may be added. Compounds capable of increasing the level of *Alcaligenes faecalis* et rel. in the small intestine may include, without limitation, substrates allowing production of nitrous and nitric oxide under low oxygen conditions in the presence of ammonia.

In an embodiment, the bacteria of the taxon *Eubacterium hallii* et rel. are bacteria from the *Eubacterium hallii* strain L2-7. The *Eubacterium hallii* strain L2-7 (DSM 17630) is available from the Deutsche Sammlung von Mikroorganismen (DSMZ). Bacteria of the taxon *Alcaligenes faecalis* et rel. may, for example, be cultured in accordance with Annamalai et al. (*Ann. Microbiol.* 2011, December, 61(4): 801-807).

The skilled person will be capable of selecting an effective amount of a compound capable of increasing the level of *Eubacterium hallii* et rel. and/or *Alcaligenes faecalis* et rel. in the small intestine using methods that are routine in the art.

All patent and literature references cited in the present specification are hereby incorporated by reference in their entirety.

It will be clear that the above description is included to illustrate some embodiments of the disclosure, and not to limit the scope of protection. Starting from this disclosure, many more embodiments that are within the scope of protection and the essence of this disclosure and that are obvious combinations of prior art techniques and the disclosure hereof will be evident to a skilled person.

EXAMPLES

Example 1

Methods

A double-blind randomized controlled trial was conducted in which the effect of a single allogenic (lean donor) microbial fecal infusion on glucose metabolism in relation to gut microbiota composition was investigated in obese subjects.

Subjects

Male Caucasian obese subjects were screened for characteristics of the metabolic syndrome comprising waist circumference >102 cm and fasting plasma glucose >5.6 mmol/1.17. Subjects with cholecystectomy and/or using any medication, probiotics and/or antibiotics in the past three months were excluded. Written informed consent was obtained from all subjects. The study was approved by the Institutional Review Board and conducted in accordance with the principles of the Declaration of Helsinki (1996). The study was registered at the online Dutch Trial Register (NTR1776).

Screening of Lean Donors

Lean Caucasian males (BMI<23 kg/m$^2$) were also recruited by newspaper advertisements. They completed a questionnaire regarding bowel habits, travel history, comorbidity and medication use. They were screened for the presence of infectious diseases according to an adapted version of the questionnaire of the Dutch Blood Transfusion service (Sanquin) (Langeveld et al., 2008, *J. Clin. Endocrinol. Metab.* 93(3):845-851). Blood was screened for the presence of antibodies to human immunodeficiency virus; human T-lymphotropic virus; Hepatitis A, B, and C; cytomegalovirus; Epstein-Barr virus; Strongyloides; and amoebiasis. Donors were also excluded if screening of their feces revealed the presence of parasites (e.g., *Blastocystis hominis* or *Dietamoeba fragilis*), *Clostridium difficile* and possible other pathogenic bacteria (*Shigella, Campylobacter, Yersinia, Salmonella*).

Experimental Design

Glucose metabolism was measured in the basal state and during a two-step hyperinsulinemic euglycemic clamp to measure endogenous glucose production (EGP), hepatic and peripheral insulin sensitivity (Rate of disposal, Rd) using [6,6 2H2]-glucose. Body weight was recorded and body composition was measured using bioimpedance analysis. Resting energy expenditure (REE) and respiratory quotient were measured using indirect calorimetry (Langeveld, *J. Clin. Endocrinol. Metab.* 2008, 93(3):845-851).

Participants were allowed to keep their own diet, but were asked to keep a weekly online nutritional diary (www.dieet-inzicht.nl) to monitor caloric intake. After an overnight fast, study subjects and donors brought freshly produced morning stool for processing; study subjects were randomized in a double-blind fashion to either allogenic (from lean male donors with BMI<23 kg/m$^2$) or autologic (own collected feces) gut microbial infusion via gastro-duodenal infusion (see procedure). Study subjects first underwent gastroduodenoscopy and small intestinal (jejunal) biopsies were taken near Treitz ligament. Biopsy samples were collected in sterile tubes, snap-frozen in liquid nitrogen and processed as described earlier (Langeveld et al., supra). A duodenal tube was positioned and bowel lavage with macrogol solution was performed over five hours to clean out endogenous fecal contamination followed by gut microbial infusion. Gastroduodenoscopy-assisted biopsies and the hyperinsulinemic euglycemic clamp were repeated six weeks after transplantation.

Hyperinsulinemic Euglycemic Clamp

After a twelve-hour fast, a catheter was inserted into an antecubital vein for infusion of stable-isotope tracer [6,6-2H2]glucose (Cambridge Isotopes, Andover, Mass.), insulin and glucose. A second catheter was inserted retrogradely in the contralateral hand vein and kept in a thermo-regulated (60° C.) clear plastic box for sampling of arterialized venous blood. Saline was infused as 0.9% NaCl at a rate of 50 mL/hour to keep the catheters patent. At t=0 hour (0800), blood samples were drawn for determination of background enrichments. Then, a primed continuous infusion of isotopes was started: [6,6-2H2]glucose (prime: 8.8 µmol/kg; continuous: 0.11 µmol·kg−1·min−1) and continued until the end of the clamp. After a two-hour equilibration period, blood samples were drawn for isotope enrichments and samples for gluco-regulatory hormones, free fatty acids (FFAs) and incretins. Thereafter (t=2.0 hours), a two-step hyperinsulinemic euglycemic clamp was started: step 1 included an infusion of insulin at a rate of 20 mU·m−2·min−1 (ACTRAPID™ 200 IU/mL; Novo Nordisk Farma BV, Alphen aan den Rijn, Netherlands) to assess hepatic insulin sensitivity. Glucose 20% was started to maintain a plasma glucose concentration of 5 mmol/L. Plasma glucose concentrations were measured every five minutes at the bedside using a Beckman glucose meter. After two hours (t=4 hours), blood samples were drawn at five-minute intervals for the measurement of glucose concentrations and isotopic enrichments. Another blood sample was drawn for measurement of gluco-regulatory hormones and FFAs. Hereafter, insulin infusion was increased to a rate of 60 mU·m−2~min−1 (step 2) to assess peripheral insulin sensitivity. After another two hours (t=6 hours), blood sampling was repeated.

Body composition was measured at baseline and after six weeks with bioelectrical impedance analysis (Maltron BF906; Maltron, Rayleigh, UK). Oxygen consumption ($VO_2$) and $CO_2$ production ($VCO_2$) were measured continuously during the final 20 minutes of both the basal state and the hyperinsulinemic euglycemic clamp by indirect calorimetry using a ventilated hood system (Sensormedics model 2900; Sensormedics, Anaheim, Calif.). REE, carbohydrate oxidation (CHO), and fatty acid oxidation (FAO) rates were calculated from oxygen consumption and carbon dioxide production. Rate of appearance (Ra) and rate of disappearance (Rd) of glucose were calculated using the modified form of the Steele equations for non-steady-state measurements as described previously. Endogenous glucose production (EGP) was calculated as the difference between Ra glucose and glucose infusion rate. Both peripheral (Rd) and hepatic insulin sensitivity (suppression of EGP) were calculated and expressed as median with range.

Gut Microbiota Analysis
DNA Isolation

DNA was isolated and purified using the repeated bead-beating plus column method as described previously (Zoetendal, *Syst. Appl. Microbiol.* 24(3):405-410). For DNA isolation of the biopsies, we used a different bead-beating protocol (Nadkarni et al., 2002, *Microbiology* 148(Pt 1):257-266). In short, 0.5 gram (wet weight) of feces was suspended in Lysis buffer (500 mM NaCl, 50 mM Tris-HCl pH 8, 50 mM EDTA, 4% SDS) plus Zirconia beads and glass beads. The tube was shaken with FASTPREP® (at setting 5.5) for three minutes at 4° C., followed by incubation at 95° C. for 15 minutes. The DNA in the supernatant was precipitated with ammonium acetate and isopropanol, washed with 70% ethanol and afterward treated with proteinase K and DNase-free RNase. Finally, the DNA was purified on a QIAAMP® spin column (Qiagen) according to the manufacturer's instructions. DNA concentration was quantified using the NANODROP® 1000 spectrophotometer (NanoDrop Technologies, Wilmington, Del.).

HITChip Microbiota Profiling

The HITChip was used for phylogenetic profiling of the microbiota in feces and small intestinal biopsies as described previously (Rajilic-Stovanojic, 2009, supra). In short, 10 ng DNA was used to amplify the 16S rRNA genes using the T7prom-Bact-27-for and Uni-1492-rev primers followed by in vitro transcription and labeling with Cy3 and Cy5, respectively, for fecal samples. The primer Prok-1369-rev was used as reverse primer for the biopsy samples because Uni-1492-rev was majorly targeting the overabundant human DNA, resulting in its depletion for efficient bacterial 16S rRNA gene amplification (data not shown). Equimolar mixes of Cy3/Cy5-labeled 16S rRNA targets were fragmented and subsequently hybridized on the microarrays at 62.5° C. for 16 hours in a rotation oven (Agilent Technologies, Amstelveen, The Netherlands), followed by washing and drying of the slides. Samples were arrayed in duplex (technical replication). After scanning of the slides, the data was extracted from the microarray images using the Agilent Feature Extraction software, versions 7.5-9.1 (on their website at agilent.com). Subsequently, the microarray data were min-max normalized and further analyzed using a set of R-based scripts (see website at r-project.org/) in combination with a custom designed relational database that runs under the MySQL database management system (see website at mysql.com). Hierarchical clustering of probe profiles was carried out using correlation-based distance and complete linkage method.

Fecal Transplant Procedure

The patient and donor delivered freshly produced stool at the day of infusion (approximately 200 grams, produced within six hours before use). Fecal samples (either allogenic or autologous) were taken before and after processing to study procedural effects on microbial composition. After delivery, the feces was covered with 500 cc sterile saline (0.9% NaCl), transferred to a blender and mixed for ten minutes. The homogenized solution was then filtered twice through a clean metal sieve. Subsequently, the filtrate was transferred to a 1000 ml sterile glass bottle and stored at room temperature until the patient had finished the bowel lavage. Finally, the fecal microbial solution was gradually infused through the duodenal tube, in approximately 30 minutes.

Biochemistry

Fasting plasma samples were obtained for measurement of total cholesterol, LDL cholesterol (LDLc), HDL cholesterol (HDLc) and triglycerides (TG), using commercially available enzymatic assays (Randox, USA and Daiichi, Japan). All analyses were performed using a Cobas Mira autoanalyzer (Horiba, France). LPS-binding Protein (LBP) and C-Reactive Protein (CRP) were measured using commercial ELISA (HyCult, USA and Roche, Switzerland). Fecal short-chain fatty acid concentrations comprising acetate, butyrate and propionate were analyzed as previously described (Wolever et al., 2000, Br. J. Nutr. 84(1):57-61).

Intestinal Microbiota and Host Mucosa Response Analyses

A morning stool sample collected at baseline and after six weeks, respectively, was obtained from donor and study subjects to determine the microbiota composition. Samples were collected into two plastic containers, immediately frozen at −20° C. and transferred to −80° C. within a week. The microbiota composition of the small intestinal biopsies and fecal samples was determined by using the Human Intestinal Tract Chip (HITChip), a custom-made Agilent microarray (Agilent Technologies, Palo Alto, Calif., USA) containing approximately 5,500 oligonucleotide probes that cover over 1,000 intestinal phylotypes (Rajilic-Stojanovic et al. 2009, vide supra). Quantification of total bacteria and methanogens was performed by 16S rRNA gene quantitative PCR with the same DNA used for HITChip analysis. Small intestinal biopsy transcriptome raw data using Human HT-12 v3 expression arrays (Illumina, San Diego, USA) were uploaded on Gene Expression Omnibus (registration number: GSE30854). Details of both intestinal microbiota and array analysis are provided in the Supplementary Appendix.

Statistical Analysis

Statistical analyses were performed with SPSS software, version 16. Data are expressed as means±standard error of mean (normal distribution) or mean (skewed distribution). To compare data between groups, Student's t-test (normal distribution) or Wilcoxon Signed rank test (skewed distribution) was used. All reported P values are two-sided. Expression analysis for the HITChip and Illumina arrays was carried out with linear mixed and random forest methods as well as canonical correlation (CCA) analysis. Statistical tests were performed using Microsoft Office EXCEL® or R statistical software (http://r-project.org/).

Statistical Analysis of HITChip and Illumina Array

Expression analysis for HITChip and Illumina array was carried out with NLME package (Pinheiro and Bates, Mixed-effect models in S and S-plus, Springer; 2000). A linear mixed model with effects for time (0 or 6 weeks), treatment (autologous or allogenic), and a cross effect of the two main effects was constructed. Repeated measures design of the experiment was taken into account by including a patient-specific random effect. For each measurement unit (gene or bacteria), contrasts were computed using the multcomp package, and the p-values thus obtained were subjected to correction for multiple comparisons by q-value package (Bretz, HTWP, Multiple Comparisons Using R, CRC Press, Boca Raton, 2010; Storey J. A., A direct approach to false discovery rates, *Journal of the Royal Statistical Society Series B* (statistical methodology) 2010, 64(3):479-498). Individual temporal stability of the fecal microbiota in the patients of both groups was determined by computing a Pearson correlation in oligonucleotide level between the samples taken at the time of the transplantation and those obtained after six weeks.

In jejunal samples, bacterial groups associated with the difference between the allogenic and autologous groups were determined with the Random Forest method using the bacterial composition changes before and six weeks after transplantation as covariates. Bootstrap averaging (bagging) (Breiman, *Bagging Predictors, Machine Learning* 1996, 24(2)) combined with redundancy analysis was then used to get a robust estimate of the groups contributing to the difference, to estimate the p-value of the separation, and to visualize the result. Association between gene expression and jejunal samples was determined using sparse canonical correlation analysis (sparse CCA). To reduce the effect of overfitting, the set of genes to be correlated consisted of top ten differentially expressed genes. The microbiota data consisted of HITChip data on six taxa found to be significantly contributing to the difference between autologous and allogenic samples in the jejunal samples. In CCA analysis, regularization parameters were first estimated with leave-one-out cross-validation. Then the model was repeated with all data, and for each variable, the correlations to the canonical variates were computed.

Results

Baseline Characteristics

A total of 44 male obese subjects were screened for features of the metabolic syndrome and 20 eligible subjects were included. Two subjects were excluded from analyses due to antibiotic use during the trial unrelated to the microbial transplant. Therefore, eighteen subjects were available for analysis.

Effect of Fecal Transplant on Insulin Sensitivity, Fecal SCFA and LBP

Seven healthy lean donors, one of which provided multiple donations, were used for the allogenic transplantation of nine obese subjects with the metabolic syndrome. Equal amounts of feces were infused in the obese subjects from either allogenic or autologous microbial fecal infusion (190±33 and 187±47 gram, ns). Moreover, the processing time between feces production and infusion did not differ (5.8±0.8 and 6.1±1.2 hours in the allogenic and autologous groups, respectively). None of the obese subjects experienced any adverse events during the trial or developed Irritable Bowel Syndrome symptoms according to the Rome III criteria.

Body weight remained stable in both groups between baseline and six weeks (allogenic: from 122.7±19 to 122.5±19 kg versus autologous: 113.2±20 to 113.4±20 kg, ns). No effect on daily caloric dietary intake, resting energy expenditure or carbohydrate/fatty acid oxidation was seen in both groups after microbial fecal infusion (data not shown). There was a marked improvement in peripheral insulin sensitivity six weeks after allogenic feces treatment (median Rd: from 26.2 to 45.3 μmol/kg/minute, p<0.05), while no significant change was observed in the autologous treatment group (median Rd: from 21.0 to 19.5 μmol/kg/minute, ns). A trend toward improvement in hepatic insulin sensitivity, expressed as EGP suppression from basal was observed (median EGP suppression: from 51.5 to 61.6%, p=0.08), while no effect was observed in the autologous treatment group (median EGP suppression: from 53.8 to 52.4%, ns). There were no changes in gluco-regulatory hormones, either in the basal state or during hyperinsulinemia (data on file) in both groups.

Lean donors were characterized by an increased fecal harvest of butyrate and propionate compared to obese participants, a trait that was also observed upon allogenic microbial fecal infusion. Moreover, we found a significant decrease of lipopolysaccharide-binding protein (LBP) six weeks after lean donor transplant (median LBP: from 19.9 to 18.6 μg/ml (p<0.05 and median CRP from 1.5 to 1.6 mg/L, ns) with no significant changes in the autologous group (median LBP: from 23.0 to 22.3 μg/ml and median CRP from 3.1 to 2.5 mg/L, ns).

Effect of Fecal Transplant on Gut Microbiota in Feces

The fecal microbiota of the obese subjects were characterized by lower gut microbial diversity, higher amounts of Bacteroidetes and decreased amounts of *Clostridium* cluster XIVa bacteria as compared to lean donor subjects (data not shown). To determine the impact of the microbial transplantation, we compared the fecal microbiota at baseline and after six weeks. Total numbers of fecal bacteria did not change following microbial fecal infusion. At six weeks, the analysis on the genus-like level showed a clear separation of the samples belonging to allogenic and autologous groups. A total of eleven bacterial groups were significantly increased (1.5-2.5 fold) upon allogenic microbial fecal infusion and contributed significantly to the separation of the groups. These include those related to the well-known butyrate-producer *Roseburia intestinalis*, the oxalate-converting *Oxalobacter formigenes*, various *Ruminococci* and other *Firmicutes*.

Effect of Fecal Transplant on Gut Microbiota in the Small Intestine

Total numbers of small intestinal bacteria did not change following microbial fecal infusion. A set of seven bacteria significantly associated with the difference in biopsies of the small intestine between the allogenic and autologous groups was detected at six weeks (Table 1). In additional analyses, a significant association (r=0.8, p<0.01) was found between small intestinal *Eubacterium hallii* concentrations and the improvement in insulin sensitivity (Rd) in human subjects with metabolic syndrome six weeks after lean donor fecal transplantation. Additionally, a significant correlation was found (r=0.6, p<0.05) between small intestinal *Alcaligenes faecalis* concentrations and the improvement in insulin sensitivity (Rd) in human subjects with metabolic syndrome six weeks after lean donor fecal transplantation. Notably, *E. hallii* was almost two-fold reduced following infusion in the autologous group. Other bacteria that were specifically increased in the autologous group in comparison with the allogenic group include ileum-inhabitants such as *Lachnobacillus bovis*, *Streptococcus bovis*, and *Prevotella ruminicola*. *Corynebacterium* spp. were reduced in the allogenic but increased in the autologous group. Finally, bacteria related to the Gram-negative *Escherichia coli* showed an almost two-fold decrease in the allogenic group and a two-fold increase in the autologous group (Table 1).

was grown in two bottles of 500 ml of Wilkins-Chalgren medium (1976, *Antimicrob. Agents Chemother.* 10:926-928) under anaerobic conditions till approximately $2 \times 10^9$ cells per ml. Subsequently, the cultures were centrifuged (10,000 rpm in 15 minutes at 4° C.), washed twice with anaerobic PBS (20 mM, pH 7, as detailed on the World Wide Web at en.wikipedia.org/wiki/Phosphate_buffered_saline) and re-suspended in 20 ml of 10% glycerol in 20 mM PBS with 20 mM glucose and 20 mM maltodextrin and frozen at −80° C. in aliquots of 100 µl containing approximately $10^{11}$ cells per ml. All manipulations were performed under anaerobic conditions.

Example 3

Eight-week-old db/db male mice on a C57BL6 background as well as male C57BL6 mice were acquired from Jackson Laboratory (Bar Harbor, Me., USA) and allowed to acclimatize at the AMC animal facility (ARIA) during two weeks before starting experiments. Mice were in a constant 12-hour light-dark cycle with controlled temperature and humidity and were given access to food (regular chow diet) and water ad libitum. Bodyweight was measured once a week. Starting at the age of ten weeks, *E. hallii* was orally administered at $10^6$, $10^8$ or $10^{10}$ CFU in 100 µl high glucose vehicle (20 mM). The solution was administered by daily oral gavage in the morning using a 21-gauge syringe for 14 days (n=8 per group). Administration of only vehicle served as control. The cultured *E. hallii* was administered orally to db/db mice (n=8 per group) for two weeks in increasing doses (10×E10/100 µl, 10× E8/100 µl and 10×E6/100 µl or dissolvens (saline+glycerol), respectively). Their effect on lipid profiles (measurement of total cholesterol, LDLc, HDLc and TG in fasting plasma samples as described in Example 1), fasting plasma glucose and insulin levels for insulin resistance (HOMA), as well as postprandial glucose (oral glucose tolerance test), are determined as described above in Example 1. Levels of short-chain fatty acids acetate, butyrate and propionate are determined in peripheral and portal blood by Mass Spectrometry (see Vrieze et al., *Gastroenterology* 2012, June 20, Epub ahead of print). Moreover, after sacrificing the mice, small intestinal and fecal samples are studied for *E. hallii* concentrations.

TABLE 1

Change in jejunal mucosal microbiota following allogenic fecal transplant (n = 9 per group).

| Phylum level | Bacterial Group | Allogenic Group Fold-change after/before transplantation | Autologous Group Fold-change after/before transplantation |
| --- | --- | --- | --- |
| Firmicutes | *Eubacterium hallii* et rel. | 1.09 | 0.61 |
| Proteobacteria | *Alcaligenes faecalis* et rel. | 1.18 | 0.97 |
| Firmicutes | *Streptococcus bovis* et rel. | 0.89 | 1.23 |
| Firmicutes | *Lachnobacillus bovis* et rel. | 0.63 | 0.98 |
| Actinobacteria | *Corynebacterium* spp. | 0.87 | 1.34 |
| Proteobacteria | *Escherichia coli* et rel. | 0.58 | 2.21 |
| Bacteroidetes | *Prevotella ruminicola* et rel. | 0.99 | 1.01 |

Example 2

*Eubacterium hallii* L2-7 as described by Barcenilla et al. (2000, *Appl. Environ. Microbiol., April*, 66(4):1654-61; DSM 17630; obtained from the laboratory of Prof. Harry Flint, Rowett Research Institute, Aberdeen, Scotland, UK)

In this experiment, we find distinct effects of short-term oral *E. hallii* L2-7 supplementation to the small intestine on normalization of insulin resistance (as detected by HOMA calculation and postprandial glucose metabolism by AUC of oral glucose tolerance curve), as well as fasting lipid profiles in db/db mice.

What is claimed is:

1. A method of treating insulin resistance and/or an insulin resistance-related complication in a human subject diagnosed with insulin resistance and/or an insulin resistance-related complication, the method comprising:
   administering to the human subject an effective amount of *Eubacterium hallii* et relatives so as to treat insulin resistance and/or an insulin resistance-related complication in the human subject.

2. The method according to claim 1, wherein the insulin resistance-related complication is selected from the group consisting of metabolic syndrome, dyslipidemia, insulin-resistance in endocrine disease, and type 2 diabetes mellitus.

3. The method according to claim 1, wherein the *Eubacterium hallii* et relatives is administered as a pharmaceutical, food, or feed composition comprising the *E. hallii* et relatives.

4. The method according to claim 3, wherein the insulin resistance-related complication is selected from the group consisting of metabolic syndrome, dyslipidemia, insulin-resistance in endocrine disease, and type 2 diabetes mellitus.

5. A method for treating insulin resistance and/or an insulin resistance-related complication in a human subject in need thereof, the method comprising:
   increasing, by an effective amount, the level of *Eubacterium hallii* et relatives in the human subject's small intestine.

6. The method according to claim 5, wherein the level of *Eubacterium hallii* et relatives in the human subject's small intestine is increased by a method selected from the group consisting of administering an effective amount of *Eubacterium hallii* et relatives to the subject and administering an effective amount of a compound capable of increasing the level of *Eubacterium hallii* et relatives in the small intestine.

7. The method according to claim 5, wherein the insulin resistance-related conditions are selected from the group consisting of metabolic syndrome, dyslipidemia, insulin resistance in endocrine disease, and type 2 diabetes mellitus.

8. The method according to claim 6, wherein the insulin resistance-related conditions are selected from the group consisting of metabolic syndrome, dyslipidemia, insulin resistance in endocrine disease, and type 2 diabetes mellitus.

9. The method according to claim 3, wherein the *Eubacterium hallii* et relatives is administered in lyophilized form.

10. The method according to claim 9, wherein the *Eubacterium hallii* et relatives are formulated with a cryoprotectant.

11. The method according to claim 3, wherein the *Eubacterium hallii* et relatives are administered in a solid dosage form.

12. The method according to claim 11, wherein the solid dosage form is selected from the group consisting of a capsule, a tablet, and a powder.

13. The method according to claim 3, wherein the *Eubacterium hallii* et relatives is administered in a liquid dosage form.

14. The method according to claim 13, wherein the liquid dosage form is selected from the group consisting of an elixir, syrup, and suspension.

15. The method according to claim 2, wherein the insulin resistance-related condition comprises insulin resistance in endocrine disease in an obese human subject having a disease selected from the group consisting of type 1 diabetes mellitus, Cushing's disease, and lipodystrophy syndrome.

16. The method according to claim 4, wherein the insulin resistance-related condition comprises insulin resistance in endocrine disease in an obese human subject having a disease selected from the group consisting of type 1 diabetes mellitus, Cushing's disease, and lipodystrophy syndrome.

17. The method according to claim 7, wherein the insulin resistance-related condition comprises insulin resistance in endocrine disease in an obese human subject having a disease selected from the group consisting of type 1 diabetes mellitus, Cushing's disease, and lipodystrophy syndrome.

18. The method according to claim 8, wherein the insulin resistance-related condition comprises insulin resistance in endocrine disease in an obese human subject having a disease selected from the group consisting of type 1 diabetes mellitus, Cushing's disease, and lipodystrophy syndrome.

19. The method according to claim 1, wherein the *Eubacterium hallii* is *Eubacterium hallii* strain L2-7 (DSM 17630).

20. A method of altering fasting plasma glucose levels in a human subject suffering from insulin resistance and/or insulin resistance-related complication, the method comprising:
   administering to the human subject an effective amount of *Eubacterium hallii* et relatives so as to alter the fasting plasma glucose levels in the subject.

21. A method of altering fasting insulin levels in a human subject suffering from insulin resistance and/or insulin resistance-related complication, the method comprising:
   administering to the human subject an effective amount of *Eubacterium hallii* et relatives so as alter the fasting insulin levels in the subject.

22. A method of altering postprandial glucose level in a human subject suffering from insulin resistance and/or insulin resistance-related complications, the method comprising:
   administering to the human subject an effective amount *Eubacterium hallii* et relatives so as to alter the postprandial glucose level in the subject.

23. The method according to claim 1, wherein the treatment of insulin resistance and/or an insulin resistance-related complication in the human subject is determined by fasting plasma glucose and insulin levels or hyperinsulinemic clamps or by utilizing an oral glucose tolerance test.

24. The method according to claim 5, wherein the treatment of insulin resistance and/or an insulin resistance-related complication in the human subject is determined by fasting plasma glucose and insulin levels or hyperinsulinemic clamps or by utilizing an oral glucose tolerance test.

* * * * *